(12) United States Patent
Barka

(10) Patent No.: US 9,541,532 B2
(45) Date of Patent: Jan. 10, 2017

(54) UV/VIS HPLC PHOTOMETER

(71) Applicant: SunChrom Wissenschaftliche Geräte GmbH, Friedrichsdorf (DE)

(72) Inventor: Günes Barka, Friedrichsdorf (DE)

(73) Assignee: SUNCHROM WISSENSCHAFTLICHE GERÄTE GMBH, Friedrichsdorf (DE)

( * ) Notice: Subject to any disclaimer, the term of this patent is extended or adjusted under 35 U.S.C. 154(b) by 145 days.

(21) Appl. No.: 14/466,088

(22) Filed: Aug. 22, 2014

(65) Prior Publication Data

US 2015/0052984 A1    Feb. 26, 2015

(30) Foreign Application Priority Data

Aug. 23, 2013  (DE) .................. 10 2013 013 975

(51) Int. Cl.
| | |
|---|---|
| *G01J 3/00* | (2006.01) |
| *G01N 30/86* | (2006.01) |
| *G01N 30/74* | (2006.01) |
| *G01J 3/28* | (2006.01) |
| *G01N 21/33* | (2006.01) |
| *G01N 30/02* | (2006.01) |

(52) U.S. Cl.
CPC ............ *G01N 30/8658* (2013.01); *G01J 3/28* (2013.01); *G01N 30/74* (2013.01); *G01J 2003/283* (2013.01); *G01N 21/33* (2013.01); *G01N 2030/027* (2013.01)

(58) Field of Classification Search
CPC .. G01N 21/314; G01N 21/33; G01N 21/3504; G01J 3/10; G01J 3/42

USPC .......................................................... 356/51
See application file for complete search history.

(56) References Cited

U.S. PATENT DOCUMENTS

| | | | |
|---|---|---|---|
| 5,917,606 A | 6/1999 | Kaltenbach | |
| 6,108,083 A | 8/2000 | Mächler | |
| 2007/0291255 A1* | 12/2007 | Larsen | G01J 3/02 356/73 |
| 2009/0039249 A1* | 2/2009 | Wang | G01N 15/0205 250/287 |

FOREIGN PATENT DOCUMENTS

| | | | |
|---|---|---|---|
| WO | WO-82/02952 | 9/1982 | |
| WO | WO 2012046096 A1 * | 4/2012 | G01N 21/05 |

\* cited by examiner

*Primary Examiner* — Tarifur Chowdhury
*Assistant Examiner* — MD M Rahman
(74) *Attorney, Agent, or Firm* — Nicholas Trenkle; Stites & Harbison, PLLC

(57) ABSTRACT

An ultraviolet-visible spectrophotometry (UV/Vis) high-performance liquid chromatography (HPLC) photometer includes a nano flow cell in which a light source feeds a reference light channel and a sample light channel, a reference photodiode for evaluating the reference light channel, and a sample photodiode for evaluating the sample light channel, which extends through the nano flow cell. To create a photometer whose signal evaluation is improved, respective effective exposure times of the sample photodiode and the reference photodiode are settable separately from one another.

4 Claims, 1 Drawing Sheet

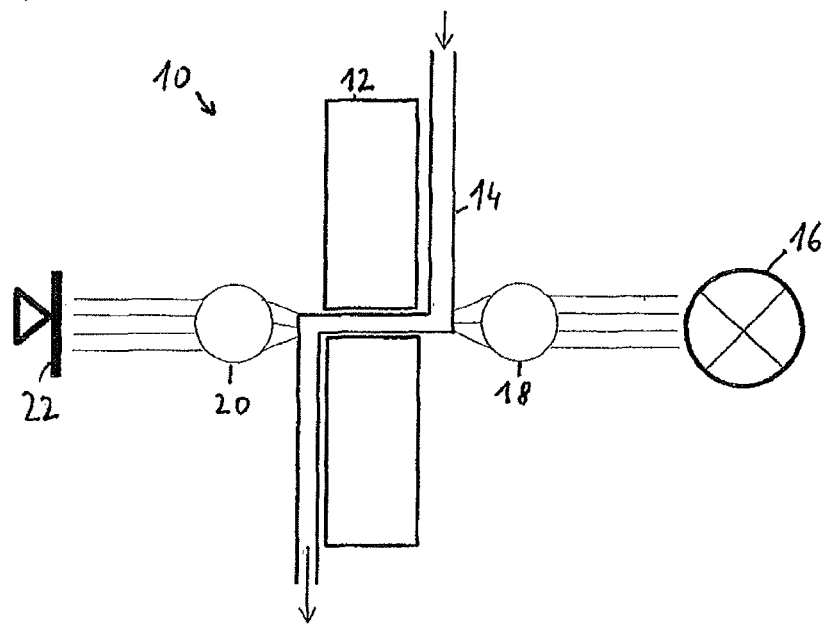

UV/VIS HPLC PHOTOMETER

FIELD OF THE INVENTION

Exemplary embodiments of the present invention relate to an ultraviolet-visible spectrophotometry (UV/Vis) high-performance liquid chromatography (HPLC) photometer having at least one nano flow cell and a light source that feeds a reference light channel and a sample light channel, in which a reference photodiode is provided for evaluating the reference light channel, a sample photodiode is provided for evaluating the sample light channel, which extends through the nano flow cell, and an evaluation device, for example, is provided for evaluating the signals of the two photodiodes.

BACKGROUND OF THE INVENTION

Normally, UV/Vis photometers in HPLC are predominantly employed in the so-called analytical scale in conjunction with a separation column having an internal diameter between 4.6 and 3 mm. In the case of columns with a smaller internal diameter, other, special flow cells are used. These cells have smaller volumes to minimize mixing and peak propagation.

If the column diameters become smaller, then the peak volumes are likewise smaller. To cleanly separate the peaks from one another, flow cells, with corresponding smaller volumes, are needed. As a result, the illuminated volume or, in other words, the volume through which light shines, and the diameter are likewise smaller. The transmission of the cell decreases, and, proportionately to this, the signal noise of the photodiodes increases.

In detection, the signal-to-noise ratio is critical. Hence the limit of detection (LOD) is located at approximately a minimum signal-to-noise (S/N) ratio of 3:1. In other words, a signal can be distinguished from the noise only whenever the ratio is at least three to one.

For a reliable limit of quantification (LOQ), an S/N ratio of at least 10:1 to 20:1 should be achieved. Some regulations even prescribe a ratio of 30:1.

At present, in cell and protein research, devices are needed that can operate with the requisite reduction in the quantity of substance. Since the substance quantity is at femtomole limits and even less, columns with a diameter of 75 μm (micrometers) or even smaller are used. In this case, only flow cells with a volume of 3 to 5 nl (nanoliters) are used.

Such cells generally comprise a quartz capillary with an internal diameter of 20 to 25 μm and an outside diameter of 280 μm. In other words, a gap of only 300 μm including the capillary course is available to the light on the way to the photodiode.

Attempts are made to compensate for this low light transmission by focusing the light, both on entering and on exiting the cell, by means of lenses. Although this does increase the quantity of light and reduces noise, the signal-to-noise ratio is nevertheless still unsatisfactory.

Commercial detectors on the market attempt to make the best of the situation by means of their internal firmware. The light coming from the optical grating is split into a reference channel and a sample channel, with the ratio of the split being invariable because of the hardware construction. The effective exposure times of the reference and sample photodiodes are usually regulated automatically such that the reference diode signal remains securely below the saturation limit. In turn, for the sample diode, this setting is inadequate for appropriately optimizing and reducing the resultant noise.

Examples of photometric devices with a flow cell are known from EP 0071645 B1, DE 695 24 405 T2, and DE 4308202 A1.

BRIEF SUMMARY OF THE INVENTION

An object of exemplary embodiments of the present invention is to improve the signal evaluation in a photometer that uses a nanocell.

In exemplary embodiments, this object can be attained by a UV/Vis HPLC photometer of the type described above, in which the effective exposure times of the sample photodiode and the reference photodiode are settable separately from one another.

By this provision, it is possible to adapt the effective exposure times of the two photodiodes used individually to the ratio of the light intensities in the two channels. As a result, the effective exposure for the sample photodiode can be set more sensitively, without the reference photodiode reaching the saturation range.

In exemplary embodiments, the setting is done such that the effective exposure time of the sample photodiode is selected to be greater than the effective exposure time of the reference photodiode. In alternative exemplary embodiments, this result can be achieved if the light intensities of the two channels are selected differently from the onset, or if diodes with different sensitivities are used.

In a further exemplary embodiment of the present invention, it is provided that measurement signal amplifiers for the signals of the reference light channel and the sample light channel can be set separately from one another in terms of their amplification factors. By this provision, the noise can be further reduced by a considerable amount. Since the digital signals moreover are far less affected by other noise sources, it is primarily the pure diode signal that is preamplified.

A further example feature for improving the signal-to-noise ratio is to provide digital software filters, which attenuate the noise, as a statistical variable, more so than the irregularly occurring measurement signals.

It has been found that the above-described provisions in combination can make it possible to reduce noise by a factor of 10 or more. Depending on individual given conditions, the user can therefore choose whether he employs the described provisions individually or if a S/N noise ratio that in the original state is especially unfavorable has to be improved by employing all the provisions. It is also possible for the noise quality to be improved only by selecting the amplification factor, only by using software filters, or by a combination of these two provisions.

BRIEF DESCRIPTION OF THE DRAWINGS

Below, one exemplary embodiment of the invention is described in further detail in conjunction with the appended drawings. In the drawings:

FIG. 1 is a schematic illustration of a nano flow cell with a sample light channel; and FIG. 2 is an illustration of an screen shot of an example user interface for receiving inputs for parameters to effect signal quality.

DETAILED DESCRIPTION OF THE INVENTION

In FIG. 1, an exemplary embodiment of a nano flow cell 10 is shown that, in simplified illustration, has a cell holder 12 and a quartz capillary 14, through which light from a light source 16 is provided for evaluating the sample flowing through the quartz capillary. In FIG. 1, only the sample light channel is shown, in order to clearly show the details involved.

Since the evaluation requires ever smaller sample volumes, the quartz capillary 14 of the nanocell 10, for an outer diameter of 280 μm, has an internal diameter of 25 μm. This means that the light gap in the cell holder 12 is only about 300 μm thick, so that only a comparatively slight amount of light can flow through the flow cell. A first collector lens 18 focuses the light from the light source 16 before it enters the light gap, while a second collector lens 20 broadens the light beam again before it strikes a sample photodiode 22. By these provisions, although the light quantity can be increased for reducing noise, the sole provision remaining is nevertheless an unsatisfactory signal-to-noise ratio.

Moreover, the photometer has a reference light channel, not shown, which is likewise supplied from the light source 16. The signal of the reference light channel is evaluated by a reference photodiode (not shown); intrinsically, this light signal is stronger, since the reference light channel does not have to be passed through the narrow light gap of a nano flow cell.

The UV/Vis HPLC detector allows the effective exposure times (that is, the integration times) of the two photodiodes to be set separately for evaluating the sample light channel and the reference light channel. The firmware, like other detectors, does set a quasi-optimal effective exposure time, but by means of the separately settable effective exposure times of the reference photodiode and the sample photodiode, the user can reduce the noise considerably by lengthening the effective exposure time of the sample photodiode.

In a second optimizing step, the user has the capability of amplifying the digital signal of the sample diode differently from the reference diode, namely to be higher (ADC range). As a result, the noise is reduced once again by a considerable amount. Since the digital signals are far less affected by other noise sources, it is primarily the pure diode signal that is amplified.

After this second step, the user has the capability of employing software filters. These are conceived of such that the noise, as a statistical variable, is attenuated markedly more so than the measurement signals occurring at irregular time intervals, which are hardly influenced by the software filter.

FIG. 2 shows a screen shot of one example of setting the parameters. The left column, "signal", indicates the values for the sample light channel, and the right column indicates the values for the reference light channel. The first line (Intensity on PA1) indicates the value for the signal intensity. In the second line (ADC range), the values for the amplification factor are indicated, and the various values are intended to show that this factor is variable; the amplification factor for the reference channel need not be higher than that of the reference channel. Primarily, in setting the amplification factor, optimizing the sample diode signal is central; the reference signal is considered to be unproblematic.

The third line (Integration time (ms)) indicates the values for the effective exposure time, which in the example shown for the sample photodiode has been set to be nearly twice as long as for the reference photodiode. The last line (Smoothing) shows the set value for the amount of filtering of a software noise filter, which here, at a scale of 1 to 9 for example, has been set to a middle value of 6.

In collaboration, the parameters described above can reduce noise significantly, by a factor of 10 or more.

The invention claimed is:

1. An ultraviolet-visible spectrophotometry (UV/Vis) high-performance liquid chromatography (HPLC) photometer, comprising:
   a nano flow cell in which a light source feeds a reference light channel and a sample light channel;
   a reference photodiode for evaluating the reference light channel; and
   a sample photodiode for evaluating the sample light channel, which extends through the nano flow cell, and
   wherein respective effective exposure times of the sample photodiode and the reference photodiode are settable separately from one another, and
   wherein reference measurement signal amplifiers for signals of the reference light channel and the sample light channel are settable separately from one another in terms of respective amplification factors for signals of the reference light channel and the sample light channel.

2. The UV/Vis HPLC photometer of claim 1, wherein the effective exposure time of the sample photodiode is set to be greater than the effective exposure time of the reference photodiode.

3. The UV/Vis HPLC photometer of claim 1, wherein the amplification factor for the signals of the sample light channel is set higher than the amplification factor for the signals of the reference light channel.

4. The UV/Vis HPLC photometer of claim 1, wherein digital software filters are provided that attenuate noise, as a statistical variable, more so than irregularly occurring measurement signals.

* * * * *